United States Patent [19]

Badia

[11] Patent Number: 4,919,658
[45] Date of Patent: Apr. 24, 1990

[54] CONNECTION FOR CATHETERS, PERFUSION UNITS AND FLASKS OF LIQUID TO BE PERFUSED

[75] Inventor: Marcelo S. Badia, Barcelona, Spain

[73] Assignee: Institute Municipal D'Assistencia Sanitaria, Barcelona, Spain

[21] Appl. No.: 201,756

[22] Filed: Jun. 3, 1988

[30] Foreign Application Priority Data

Jun. 5, 1987 [ES] Spain .............................. 8701910[U]

[51] Int. Cl.⁵ ............................................ A61M 25/00
[52] U.S. Cl. .................................... 604/265; 604/199; 604/411; 604/905
[58] Field of Search ........ 604/199, 265, 262, 411–416, 604/905

[56] References Cited

U.S. PATENT DOCUMENTS

| 2,416,391 | 2/1947 | Hixson | 604/411 X |
| 2,911,123 | 11/1959 | Saccomanno | 604/411 X |
| 3,354,881 | 11/1967 | Bloch | 604/198 |
| 3,542,240 | 11/1970 | Solowey | 604/411 X |
| 3,902,489 | 9/1975 | Carter | 604/411 |
| 4,201,208 | 5/1980 | Cambrio | 604/262 X |
| 4,416,663 | 11/1983 | Hall | 604/199 X |

FOREIGN PATENT DOCUMENTS 1337891  8/1963  France ................................ 604/411

Primary Examiner—Dalton L. Truluck
Attorney, Agent, or Firm—Cushman, Darby & Cushman

[57] ABSTRACT

Connection for catheters, perfusion units and flasks containing liquids to be perfused, of the kind used when parenterally administering liquids, principally characterized in that it comprises a chamber containing an antimicrobian product between the components to be connected, that is to say, between the outlet of the container containing the liquid to be perfused and the perfusion unit, or between this latter and the entrance to the catheter, a hollow needle which traverses opposed penetrable wall portions of the chamber and the antimicrobian liquid therein.

7 Claims, 6 Drawing Sheets

FIG. 6
FIG. 7
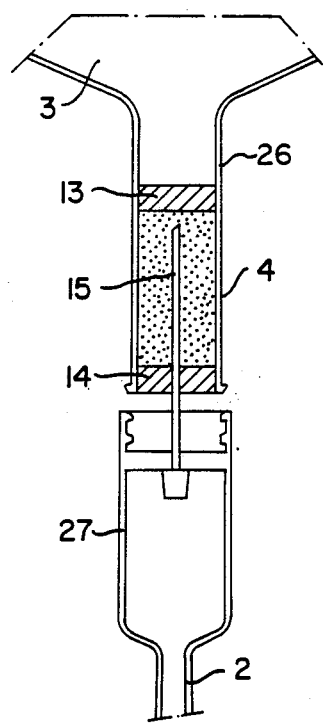
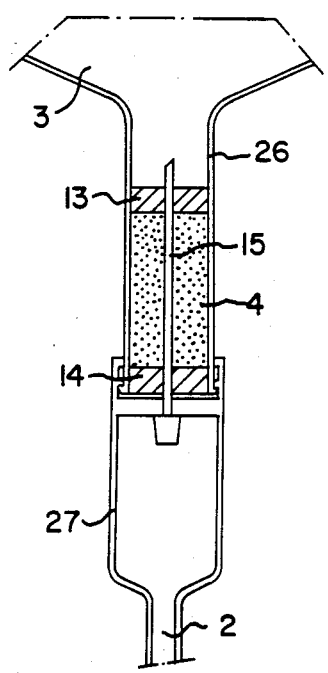

CONNECTION FOR CATHETERS, PERFUSION UNITS AND FLASKS OF LIQUID TO BE PERFUSED

This invention relates to a connection for catheters, perfusion units and flasks basically designed for administering liquids to be perfused parenterally for clinical controls or diagnostic techniques.

It is already known that the supply of serum for patients in emergency units or undergoing different medical treatments comprises the use of a container for the liquid in question with a flexible duct or perfusion unit, which also goes to the catheter applied to the patient's body. Experience has shown that where the catheter is connected to the perfusion unit, or this latter to the container holding the liquid to be perfused, cases of contamination by microorganisms of different types occur when the catheter is sued for clinical controls or for diagnostic techniques.

The connection that constitutes the object of this invention eliminates risk of contamination from microorganisms, preventing, in case they are present in the connection components between the container and the catheter, any infection and ensuring that the ducting between the containers and the patient's body, including the catheter itself, remains free from infection by said microorganisms.

To these ends, the connection herein described comprises a component capable of reducing the number of viable microorganisms so that even if these were to reach the exterior of a connection component, the patient would remain free from contamination and from any possible resultant infection.

The component which reduces the quantity of microorganisms that may be present consists of a capsule holding an antimicrobian product capable of neutralizing the action of microorganisms. Said product could be, for example, iodine alcohol or similar. The capsule is a chamber having two opposed end walls made of a flexible material like, for example, rubber, gum, etc., producing a water-tight seal which allows for penetration with a needle and which can be traversed by a tubular needle, with or without an internal mandril, and constitutes part of the connection component associated with the duct coming from the container containing the serum or biological liquid to be administered.

The device described herein may be applied in different ways which shall be expounded on in the description below and illustrated in the accompanying drawings which show some of the different embodiments of the invention, as per the principles of the claims.

BRIEF DESCRIPTION OF THE DRAWINGS

FIG. 1 shows three intravenous serotherapy units, of which the first has, at the discharge, formed by the container's or flask's lower mouth, a device which is an object of this invention. The second container or flask, conventionally configurated, has an outlet duct in the middle of which is a connection device embodying the invention, for lateral addition of solutions to the duct. The third container or flask, also conventional, has, coupled to the infusion unit connection with the catheter, a device which is the object of this invention. These three utility units may be employed simultaneously or alternately.

FIGS. 6 and 7 show use of the device of this invention with a flexible flask of the kind used for parenteral nutrition, made of polyethylene of example, which does not require air to flow in.

Figures 1A, 1B, 1C, 2, 3:
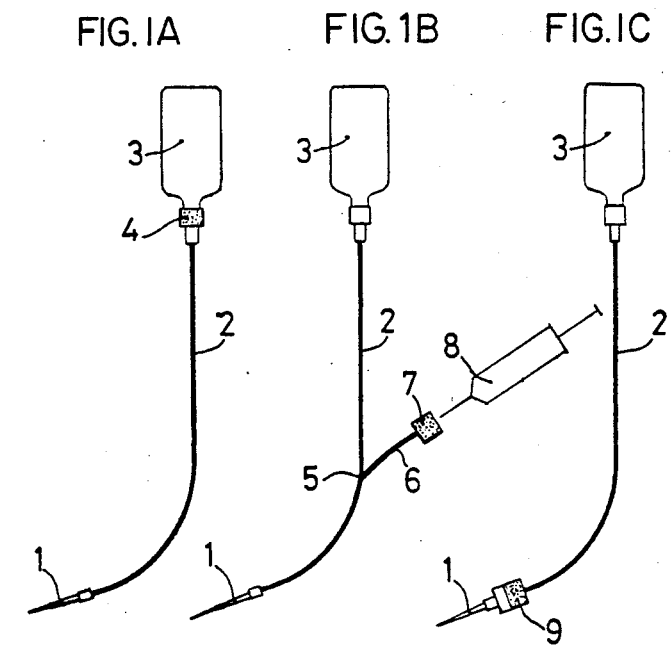
FIG. 2 shows the application of the connection device with a syringe to be inserted to the mouth of a catheter the outlet end of which goes to the patient's body and which is used to administer medicines or other solutions. It may also be used to connect control or diagnostic units.
FIG. 3 shows the neutralizing connection device fitted at the mouth of a flask that is filled with a syringe to minimize infection risk, and from which the solution to be perfused is to be extracted.

The cathether or tubular duct 1 to be attached to the patient's body is conventionally connected to a flexible duct 2, called a perfusion unit, which is connected to the outlet of the container or flask 3 which contains the serum or liquid to be perfused. In the first arrangement shown in FIG. 1, the device 4 reduces the quantity of microorganisms that could have contaminated the duct connection to the flask 3 on making the connection In the second arrangement shown in FIG. 1, the perfusion unit 2 is connected at a point 5 intermediate its ends to a secondary duct 6. The inlet end of this secondary duct is fitted with a device 7 embodying this invention and through which, by means of a syringe 8, additional solutions may be administered. In the third arrangement shown in FIG. 1, the outlet end of the perfusion unit 2 is joined to a device 9 embodying this invention directly before the catheter, i.e. at the inlet end thereof, which is to be attached to the body of a patient.

FIG. 2 shows an arrangement in which a syringe 8 is applied to the device 7 attached to the inlet end of a duct 6 constituting an accessory duct, as in the arrangement shown in FIG. 1 or, as in another arrangement in which a syringe 8 is attached to the catheter itself 1 or to a control or diagnostic unit. In the arrangement shown in FIG. 3, the syringe 8 extracts liquid from a container 10, in the mouth of which the device 11 (the same as aforementioned numbers 4, 7 and 9) is fitted.

Figure 8:
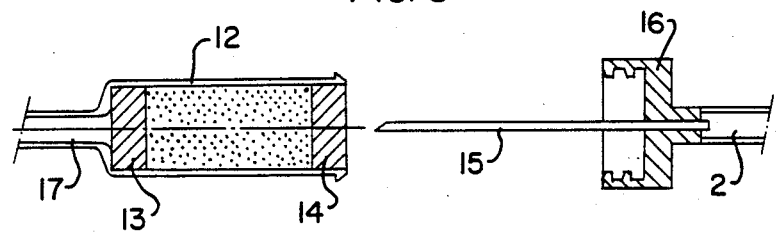
FIGS. 8, 9 and 10 show the connection device being used at the point at which the infusion unit and the catheter are connected, as per the third unit illustrated in FIG. 1.
Figure 9:
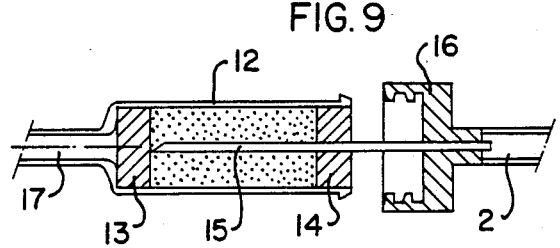
Figure 10:
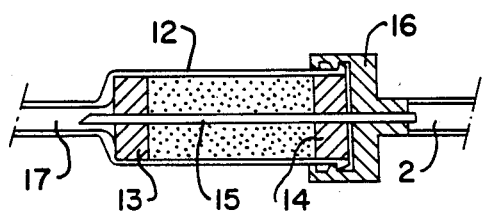

As shown in FIGS. 8–10, the device in question comprises, for each of the above-mentioned arrangements, a chamber containing antimicrobian material within a cylinder 12 made of glass, rigid or semi-rigid polyethylene or other plastic material with, in a preferential version, rubber plugs 13 and 14 in each end. These plugs may be penetrated by a tubular needle 15, with or without an interior mandril, which forms part of a connection component 16 associated with duct 2, for the above-mentioned arrangements. One end of the chamber is unobstructed so that the plug thereof, e.g. the plug 14, is accessible so that it may be penetrated by the needle 15. the other end of the chamber constitutes the continuation of a liquid duct 17. The plugs 13 are spaced apart at a distance so that both may be penetrated by the needle as shown in FIGS. 8 and 9.

Figure 4:
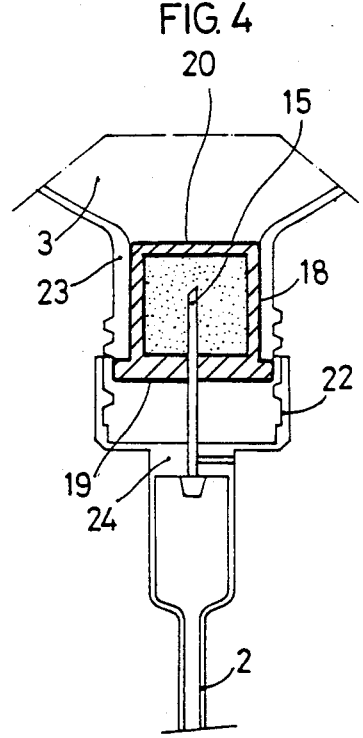
FIGS. 4 and 5 show the connection device being used with a rigid flask, glass for example, of the kind used for serotherapy and which requires air to enter simultaneously in order to allow the liquid to flow out.
Figure 5:
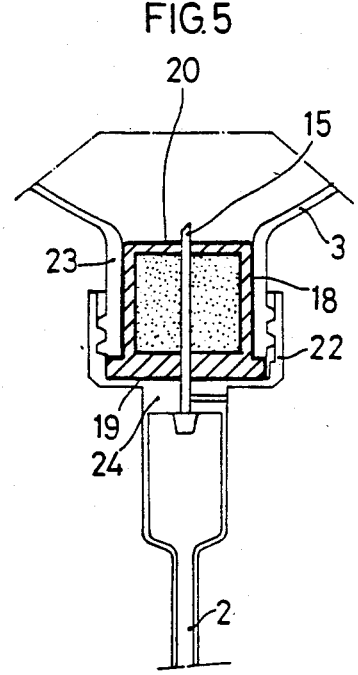

In the case of a rigid flask or container made of glass for example, as shown in FIGS. 4 and 5, a cylindrical rubber device 18 is applied to the lower opening of the container 3. One of the closed ends of this device, marked 19, will be penetrated by the tubular needle 15, with or without a mandril therein, which, after traversing the end 19, will perforate the other end 20 until it reaches the inside of the container 3, where it may collect the liquid to be perfused.

It is here that while the needle 15 is traveling for whatever time may be necessary, through the inside of the chamber that contains an antimicrobian product, in any form, liquid, gas, etc. (for example the aforementioned iodine alcohol), any contaminating microorganisms that may be in the several connection components are reduced.

In the arrangement shown in FIGS. 4 and 5, the connection device comprises a screw cap 22 connected to one end of duct 2 and which screws on to the threaded mouth of the flask or container 3, and in the cap carries the tubular needle 15 the base of which is attached to and extends through a partition 24.

FIGS. 6 and 7 show an arrangement wherein the flask 3 is made of a flexible material with an elongated rigid mouth 26. The device 4 is of the general type herein described, with a rigid cylinder and flexible end plugs 14, 13, traversed, one after the other, by the needle 15 carried by the connection component 27.

Figure 11:
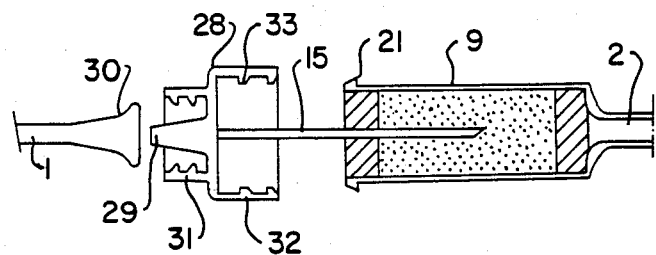
FIGS. 11 and 12 show another arrangement in which the connection device is used at the junction between the inlet end of the catheter and the duct coming from the flask containing liquid to be perfused.
Figure 12:
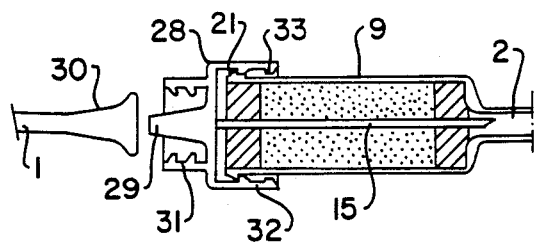

FIGS. 11 and 12 show the connection device for use with an adaptor 28 for catheters already in place. In these Figures the linking method between the adaptor 28, connecting the inlet end 30 of the catheter 1 to the chamber within the device 9, as per the third arrangement shown in FIG. 1, can be observed. The adapter 28 has an axial protuberance 29 on which the wide mouth 30 of the catheter 1 fits and a cylindrical part 31 which surrounds that mouth. Another cylindrical part 32, of a larger diameter, has interior threads 33 which engage an annular protuberance 21 on the end of the device 9.

Figure 13:
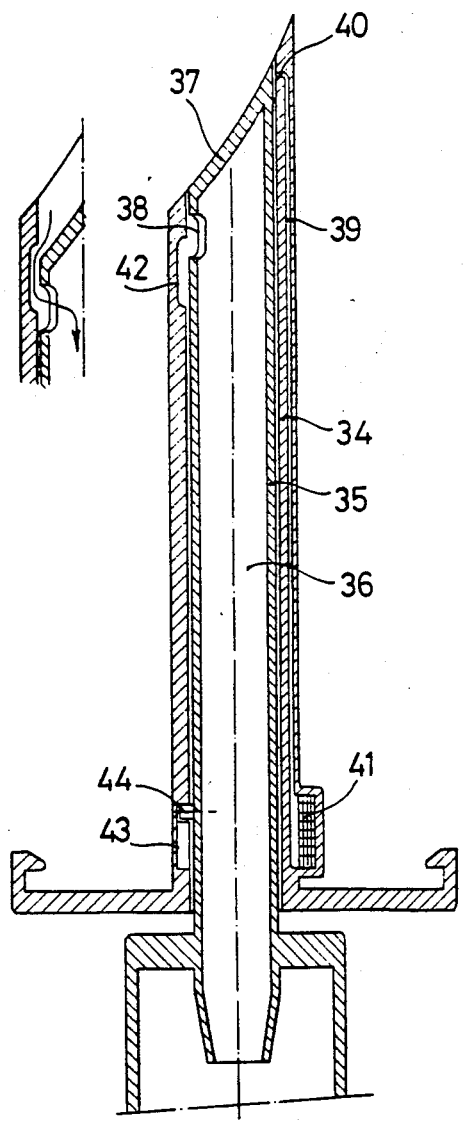
FIG. 13 shows an example of a needle to be used with the connection device, which has an internally fitted mandril.

FIG. 13 shows an example of a connection needle 34 fitted with an internal mobile mandril 35, the central part 36 of which is hollow with the forward end 37 closed and a lateral opening 38 near to the closed end. The wall of the needle 34 has a longitudinal duct 39 to allow air to pass to an outlet 40 at the forward end of the needle. This external air is filtered before entry, through filter 41 of the inlet end of the duct 39. The inside of the needle 30 has a recess 42 adjacent the forward end and another 43 at the base end into which projects a stop 44 on the mandril, limiting the extent of the mandril's axial movements. When the mandril is in the closed position, its end 37 blocks the needle outlet, so preventing any liquid escaping When the mandril is subjected to a rearward axial movement, the liquid flows through the inside of the mandril and out through opening 38 and when the end 37 of the mandril 37 is retracted sufficiently to expose the needle cavity 42, liquid flows out of the needle.

The results of experiments carried out with the device described herein are completely positive in that the presence of any microorganisms on the exterior of the tubular needle 15 or the exterior of components 16, 14 or 18, as per the different arrangements herein described, reduces the number of viable microorganisms, avoiding any possible effect they may have.

It is stated that everything not affecting, altering, changing or modifying the essence of the connection herein described shall be variable for the purposes of the present invention.

I claim:

1. Connection means for connecting catheter units to perfusion units or perfusion units to container units containing liquids to be perfused, especially liquids used for parenteral administration, comprising:
    wall means defining a chamber containing an antimicrobial product adapted to be connected between two of said units, i.e. between the outlet of the container and a perfusion unit or between the latter and the inlet of a catheter, said wall means having opposed portions sealingly penetrable by a hollow needle, said wall means being attached to one of said two units with one of said wall portions being exposed to the interior of said one unit;
    rigid coupling means detachably connectable to said wall means and extending over the other of said wall portions, said coupling means being adapted to be connected to the other of said two units; and
    means defining a flow path through said coupling means for flow of liquid between said two units, said path including a hollow needle having its base secured to said coupling means, the length of said needle being greater than the distance between the outer sides of said opposed wall portions, and said needle being positioned to penetrate both of said wall portions when said coupling means is connected to said wall means.

2. Connection means according to claim 1, wherein the wall means is located within the outlet mouth of a container and consists of a one piece hermetically sealed body and the needle has a duct extending longitudinally through the wall of said needle from the tip thereof to its base to allow external air to pass into the container.

3. Connection means according to claim 1 wherein the container is made of a flexible material and the wall means defines a rigid tubular connector coupled to the mouth of said container.

4. Connection means according to claim 1 including an auxiliary duct attached to an intermediate point on the perfusion unit and wherein the wall means is attached to the inlet end of said auxiliary duct.

5. Connection means according to claim 1 wherein the coupling means is detachably connectable to the inlet end of the catheter .

6. Connection means according to claim 1, wherein the antimicrobian product is a solution of iodine alcohol.

7. Connection means according to claim 1 including a mandril within the hollow needle to open or close the outlet at the needle tip.

* * * * *

UNITED STATES PATENT AND TRADEMARK OFFICE
CERTIFICATE OF CORRECTION

PATENT NO. : 4,919,658
DATED : April 24, 1990
INVENTOR(S) : Marcelo SEGURA BADIA It is certified that error appears in the above-identified patent and that said Letters Patent is hereby corrected as shown below:

On the Title Page:

[75] Inventor: Marcelo Segura Badia, Barcelona, Spain

[73] Assignee: Institut Municipal D'Assistencia Sanitaria, Barcelona, Spain (part interest)

Signed and Sealed this

Twenty-second Day of December, 1992

*Attest:*

DOUGLAS B. COMER

*Attesting Officer*     *Acting Commissioner of Patents and Trademarks*